(12) United States Patent
Nur et al.

(10) Patent No.: US 8,322,637 B2
(45) Date of Patent: Dec. 4, 2012

(54) METHOD OF MICRONIZATION

(75) Inventors: Israel Nur, Moshav Timorim (IL); Liliana Bar, Rehovot (IL)

(73) Assignee: Omrix Biopharmaceuticals Ltd., Nes-Ziona (IL)

( * ) Notice: Subject to any disclaimer, the term of this patent is extended or adjusted under 35 U.S.C. 154(b) by 420 days.

(21) Appl. No.: 12/312,221

(22) PCT Filed: Oct. 30, 2007

(86) PCT No.: PCT/IL2007/001318
§ 371 (c)(1),
(2), (4) Date: Apr. 30, 2009

(87) PCT Pub. No.: WO2008/053475
PCT Pub. Date: May 8, 2008

(65) Prior Publication Data
US 2010/0068196 A1    Mar. 18, 2010

Related U.S. Application Data

(60) Provisional application No. 60/856,042, filed on Nov. 2, 2006.

(51) Int. Cl.
*B02C 19/06* (2006.01)
(52) U.S. Cl. .................................... 241/5; 241/29
(58) Field of Classification Search ............... 241/5, 39, 241/29
See application file for complete search history.

(56) References Cited

U.S. PATENT DOCUMENTS

| | | | |
|---|---|---|---|
| 4,502,641 A | | 3/1985 | Coombe |
| 5,021,554 A | * | 6/1991 | Thompson .......... 530/399 |
| 5,354,562 A | | 10/1994 | Platz et al. |
| 5,855,326 A | | 1/1999 | Beliavsky |
| 6,789,756 B2 | * | 9/2004 | Beliavsky .......... 241/5 |
| 7,326,294 B2 | * | 2/2008 | McCausland et al. .......... 117/70 |
| 2003/0155454 A1 | | 8/2003 | Beliavsky |
| 2004/0121003 A1 | | 6/2004 | Chickering, III et al. |

FOREIGN PATENT DOCUMENTS

| | | |
|---|---|---|
| EP | 0384752 | 8/1990 |
| EP | 0534178 | 4/2001 |
| EP | 1390485 | 10/2006 |
| WO | WO 94/08719 | 4/1994 |

OTHER PUBLICATIONS

Brochure for 'Micronizer® Jet Mill' Sturtevant 2000 [on-line][Found on May 18, 2011]http://www.sturtevantinc.com/brochures/Sturtevant_Micronizer.pdf>.
International Search Report re: PCT/IL2007/001318 dated Feb. 19, 2008.
Office Action issued by Russian Patent Office re: dated May 26, 2011.

* cited by examiner

*Primary Examiner* — Mark Rosenbaum
(74) *Attorney, Agent, or Firm* — David R. Crichton

(57) ABSTRACT

A method for micronization of a dispersion of particles including a protein having a predetermined level of biological activity, is provided. The method includes introducing the dispersion into a vortex chamber milling apparatus under milling conditions which result in a protein powder having a particle size distribution of 5 to 100 μm and/or exhibiting a 30 to 400 fold size reduction of the protein particle dispersion from its original size, and retaining at least 80% of the predetermined level of biological activity of the protein. The milling conditions include one or more parameters selected from the following: input pressure between 1 and 7 Bars; injector pressure between 0.2 and 5 Bars; loading rate between 0.1 and 5 kg/hour; and gas flow between 30 and 100 m³/hour.

17 Claims, 3 Drawing Sheets

US 8,322,637 B2

METHOD OF MICRONIZATION

This is a National Phase Application filed under 35 U.S.C. 371 as a national stage of PCT/IL2007/001318, with the filing date of Oct. 30, 2007, an application claiming the benefit under 35 USC 119(e) U.S. Provisional Patent Application No. 60/856,042, filed on Nov. 2, 2006, the entire content of each of which is hereby incorporated by reference in its entirety.

FIELD OF THE INVENTION

This invention relates to a method for reducing the particle size of protein powders.

BACKGROUND OF THE INVENTION

In recent years, a need has arisen for the manufacture of pharmaceutical powder dispersions of micron and sub-micron particle size having a controlled, narrow particle size distribution. Applications for such powders include, for example, pharmaceutical aerosol delivery by dry powder inhalers, increasing bioavailability of water insoluble drugs and haemostatic devices composed of a biodegradable composite matrix into which lyophilized powders of clotting factors are impregnated. The process of milling a powder to micron and sub-micron particle size is known as micronization.

Among the known micronization methods are methods which involve high shear rates and high energy inputs, such as jet milling or pulverizing systems, ball milling, high-pressure homogenization and microfluidization. Such methods are generally incompatible with biological molecules which are sensitive to thermal and/or physical degradation. Other, gentler, known methods include spray drying, recrystallization, emulsion-solvent extraction and methods using supercritical fluids such as Rapid Expansion of Supercritical Solutions (RESS).

Whirl or vortex chambers for milling are also known. For example, U.S. Pat. No. 4,502,641 discloses a combination of the jet milling principle with a vortex chamber. There are also known milling vortex chambers which perform a so-called resonance whirl milling. WO 94/08719 describes a whirl chamber milling apparatus fitted with tangential fluid injection nozzles which performs a so-called "resonance vortex grinding".

U.S. Pat. No. 5,855,326 to Beliaysky, whose entire contents are incorporated by reference, discloses a whirl milling chamber for fine comminution of a particulate solid material, the chamber being formed in a housing having a substantially cylindrical shape with two end faces and a side wall provided with one or more tangential nozzles for the injection of a working fluid into the chamber and creating a vortex therein, said chamber comprising means for the introduction there into a particulate solid material to be comminuted, an axially disposed discharge passage provided in one or both said end faces, and control means in the form of one or more mechanical elements adapted to interact, when the vortex is created, with its layers moving close to inner walls of the chamber, thereby enabling for control of the comminution. Operation of the whirl chamber is exemplified in the patent using sand.

U.S. Pat. No. 6,789,756 to Beliaysky, whose entire contents are also incorporated by reference, discloses an improved vortex mill for milling a substantially particulate solid material, which includes one or more working chambers. The mill also includes one or more working fluid inlets and one or more discharge ports. One or more working fluid inlets together with one or more discharge ports facilitate the vortex flow within the one or more working chambers. There are also one or more feed inlets to provide milling of the solid material, which is discharged from one or more discharge ports. In addition, there is an apparatus for inducing controlled perturbations in the flow of the working fluid in the one or more working chambers, thereby to improve the milling of the solid material in the vortex flow.

The Hercules fibrin fleece is a haemostatic device composed of a biodegradable composite matrix of non woven Vicryl™ knitted into woven Oxidized Regenerated Cellulose (ORC, Interceed™), into which lyophilized powders of fibrinogen and thrombin are impregnated via a suspension in a volatile solvent.

SUMMARY OF THE INVENTION

The object of the present invention is to provide a mechanized method for micronization of a protein particle dispersion to a defined particle size distribution while substantially retaining the protein activity.

The present invention provides a method for micronization of a dispersion of particles comprising a protein having a predetermined level of biological activity, the method comprising introducing the dispersion into a vortex chamber milling apparatus under milling conditions which result in a protein powder having a particle size distribution of 5 to 100 µm and retaining at least 80% of the predetermined level of biological activity of the protein, wherein the milling conditions include one or more parameters selected from: input pressure between 1 and 7 Bars; injector pressure between 0.2 and 5 Bars; loading rate between 0.1 and 5 kg/hour; and gas flow between 30 and 100 $m^3$/hour.

The method of the invention advantageously allows obtaining protein powder having a consistent and controlled particle size distribution.

In one embodiment of the present invention, the particles of the initial protein particle dispersion are a priori produced to have cracks or cavities or other structural imperfections that constitute weak points which may aid in disintegrating the particle in the milling process. In one embodiment, the protein particle dispersion is prepared by a freeze-drying process such as lyophilization. Lyophilization is typically carried out by freeze-drying and involves the removal of water from a frozen cell suspension by sublimation under reduced pressure. Alternative dehydration processes which extract water from protein material are also well known in the art of protein powder production and can be used. In a further embodiment the freeze dried dispersion is mechanically crushed before milling. In a still further embodiment of the invention the dispersion is mechanically crushed to particles that passed through a 2 mm SS sieve.

The protein treated in the method of the invention has a biological activity, i.e. an activity having an effect on one or more physiological processes in the human body. For example, the protein may be an enzyme and the corresponding biological activity would be the enzymatic-catalytic activity of the enzyme. Non-limiting examples of proteins which may be used in the invention include any protease in the clotting cascade and its protease substrate; proteins in the complement cascade and its contra part; growth factors and their receptors; hormones and their receptors; immunoglobulins; anabolic and catabolic enzymes; enzymes that catalyze the following biochemical reactions: phosphorylation, dephosphorylation carboxylation, annealing, proteolysis, trans-amination, deamination, oxidation, hydrogenation, hybridization, hydrolysis, isomerization, inversion, glycolysis, DNA and RNA polymerization, esterification, etc. In one embodiment, the protein is a clotting factor and the biological activity is clotting activity. In another embodiment, the protein is thrombin or fibrinogen. The protein can be a mixture of one or more of said proteins. In one embodiment of the invention, the protein is Bac2. In another embodiment of the invention, the protein is thrombin.

The protein may be synthetic, naturally occurring, prepared by transgenic or recombinant methods, including processed, denatured or otherwise modified protein.

The level of biological activity may be predetermined by standard biological assays as are well known to the skilled man of the art. For example, if the protein is an enzyme, its biological activity can be determined by carrying out one or more assays which measure the activity. In a specific example, to determine the clotting activity of fibrinogen, the Clauss assay may be used (to a suitable volume and dilution of the fibrinogen sample maintained at 37° C., a solution of human thrombin [approx. 20 IU/ml and containing at least 1 mmol/litre of calcium] is added; the clotting time is determined and the activity is calculated against a calibration curve prepared using an appropriate fibrinogen standard), or clottable fibrinogen may be determined by measuring absorbance at 280 nm. In another specific example, clotting activity of thrombin may be determined by the clotting method (to a suitable volume and dilution, a fibrinogen solution [1 g/l of clottable protein] warmed to 30° C. is added and the clotting time is measured immediately. The activity of the test preparation is calculated against a calibration curve prepared with a reference preparation of thrombin).

The vortex chamber milling apparatus used in the invention preferably comprises tangential fluid injection nozzles and performs resonance whirl milling using pressure gradients. It is believed that the rapid gas pressure changes in the vortex chamber cause disintegration of the particles along their planes of weakness. In one embodiment, the mill apparatus is as disclosed in U.S. Pat. No. 5,855,326. In another embodiment, the mill apparatus is as disclosed in U.S. Pat. No. 6,789,756. One example of such a milling apparatus is the Super Fine Vortex Mill™ (SFVM) manufactured by Super Fine Ltd. of Yokneam, Israel (shown schematically in FIG. 6).

The milling conditions may include one or more of the following parameters:
  (a) Pressure of the incoming flow of the dispersion into the mill (=input pressure)—will generally be between 1 and 7 Bars, with the lower limit being within the range of 1-3 Bars (e.g. 1, 2 or 3 Bars) and the upper limit being within the range of 4-7 Bars (e.g. 5, 6 or 6.3 Bars);
  (b) Pressure at the feeding injector (=injector pressure—in cases where an injector is used for feeding*)—will generally be between 0.2 and 5 Bars. In one embodiment of the invention, the injector pressure is 2 Bars;
  (c) Loading rate—will generally be between 0.1 and 5 kg/hour, with the lower limit being within the range of 0.1-2 kg/hour (e.g. 0.2, 0.4, 0.6 or 1.6 kg/hour) and the upper limit being within the range of 3-5 kg/hour (e.g. 2.4, 2.8, 3.0, 3.7 or 4.2 kg/hour); and
  (d) Gas flow from the fluid injection duct to the discharge duct (=gas flow**)—will generally be between 30 and 100 m³/hour (e.g. 35, 40, 50, 58, 60, 69, 70, 80 or 90 m³/hour).
    *The incoming flow of the dispersion is usually high and the vacuum formed in the mill sucks the powder into the chamber. Because the incoming flow in the method of the invention is relatively low, there is not enough suction of the powder into the chamber and therefore a feeding injector is often needed.
    **Any inert gas may be used in the gas flow from the fluid injection duct to the discharge duct (dry air, argon, nitrogen, etc.). In the examples below, air is used.

In another embodiment of the invention, the resulting protein powder has a particle size distribution of 5 to 100 μm, with the lower limit being 5, 10, 15 or 20 μm and the upper limit being 45, 50, 55, 60, 65, 70, 75, 80, 85, 90, 95 or 100 μm. In a further embodiment, the size of at least 90% of the particles, more preferably at least 95%, most preferably at least 97%, is within the particle size distribution. In a further embodiment of the invention, the protein powder retains at least 80%, more preferably at least 90%, most preferably at least 95%, of the predetermined biological activity.

In a still further embodiment, the micronization results in a 30 to 400 fold size reduction of the protein powder from its original size.

The disclosure of ranges is easily understood by the skilled person. It means the disclosure of continuous values and figures between the limits of the ranges, including the limiting figures and values. For example, if a range is given of from 1 to 7, it is meant at least 1, 2, 3, 4, 5, 6, or 7 with all combinations of intermediate sub ranges such as 1 and 2, 1-3, 1-4, 1-5, 1-6, or 1-7 and 2 and 3, 2-4, 2-5, 2-6, or 2-7 and so on.

The entire disclosure of all applications, patents and publications, cited above or below, is hereby incorporated by reference.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

Figure 1:
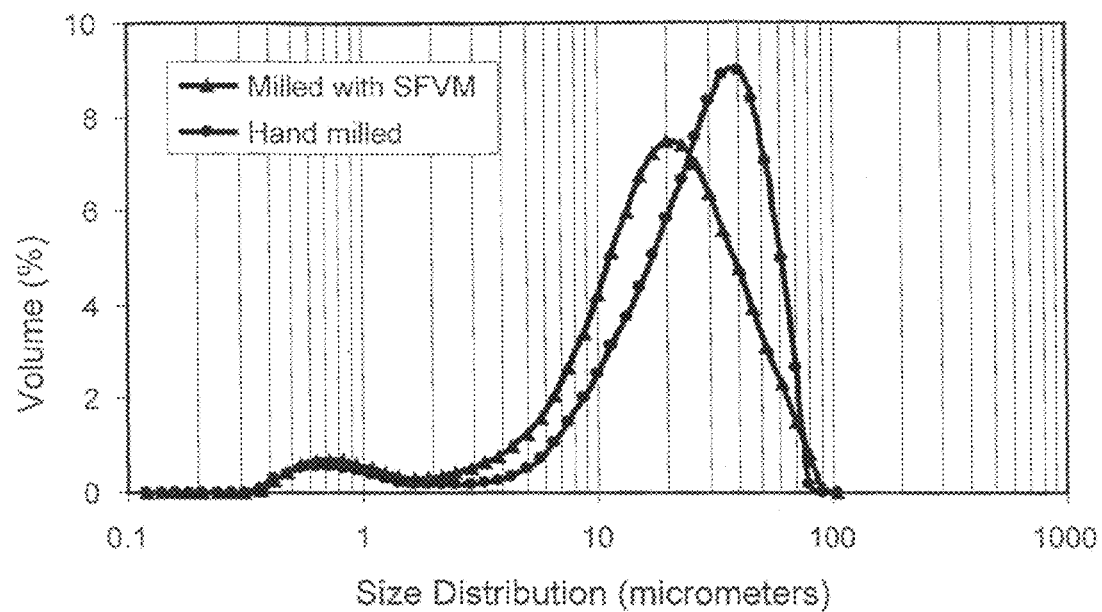
FIG. 1 shows a comparison of the size distribution profile of human fibrinogen2 powder, hand-milled versus SFVM.

An exemplary embodiment of the invention will be described with respect to the SFVM, produced by Super Fine Ltd. Yokneam, Israel. It is to be understood, however, that the invention may be practised with other types of milling machines in accordance with the invention.

I. Materials

Biological Product

All batches of the biological products—human fibrinogen2 and thrombin—were lyophilized in PFI, Tel Hashomer, Israel. Human fibrinogen2 (also referred to at times as BAC2) is a concentrated viral-inactivated cryoprecipitate of human plasma (the cryoprecipitate is typically prepared as described in EP 534,178) which consists mainly of fibrinogen (approx. 85%) and is plasminogen-depleted (the removal of plasminogen is typically carried out as described in EP 1,390,485) and without anti-fibrinolytic agents added. The biological product arrived as a lyophilized cake in a LyoGuard® plastic tray double wrapped with an aluminum foil pouch and a thick polyethylene bag. The double wrapped trays were kept at 2-8° C. until milled.

Carrier

Hydrofluorocarbon (HFE)-7000 was used as carrier of the biological product. However, the biological material can be suspended in any suitable solvent, and HFE is only a non limiting example.

II. Methods

The biological products were lyophilized in LyoGuard®. All LyoGuards were filled with 1.5 liters of either human fibrinogen2 or thrombin. The dry, lyophilized products were transferred to the testing facility wrapped in aluminum foil. At the testing site, the foil wraps were opened and the cake was first crushed mechanically by spatula against a SS sieve of 2 mm, and then the coarse powder was fed into the SFVM via a conveyer. The pressure of the injector and the miller was pre-set before loading the product, and fine-tuned to the desired pressure during the operation. The loading rate was maintained by pre-weighing the product in aliquots; the load of each aliquot was carefully timed. The powders were collected in glass jars attached to the end of the cyclone SS funnel.

The following tests for determining biological activity and physical parameters were performed:
1. Water content—Karl Fisher
2. Particle size distribution—Particle size distribution can be measured with a Beckman Coulter LS 13 320, which allows determining the particle size distribution of a powder either in a liquid or in dry powder form by using the principles of light scattering. The coulter allows measuring particle sizes in the range of 0.375 μm-2000 μm, conducted in powder dispensed in HFE7000.
3. Fibrinogen clotting activity—Clauss assay [described above].
4. Clottable fibrinogen by absorbance at 280 nm—To quantitatively determine the clottable fibrinogen, the tested sample is mixed with Thrombin and a clot is formed. Sodium-EDTA is used as a chelator of the reaction cofactor ($Ca^{++}$) and inhibits the activation of FXIII to FXIIIa (plasma-transglutaminase) by thrombin, thus preventing the formation of gamma-glutamyl-epsilon-lysine bridge of non-clottable protein to fibrin. These non-clottable proteins which are not cross-linked to the fibrin network are removed by first drying the clot on a filter paper, followed by successive washes with saline. Subsequently the clot is solubilized in urea/NaOH solution and quantification of clottable fibrinogen is done by measurement at 280 nm (after reduction of light scattering at 320 nm) against a known internal standard.
5. For the determination of total protein, clottable fibrinogen, fibrinogen determination by Clauss and for the determination of thrombin potency by clotting time in lyophilized and/or milled samples of fibrinogen and thrombin, respectively, the powders should be resuspended in a suitable buffer solution.
6. Thrombin activity by the clotting method [described above].

III. Results

The SFVM uses rapid gas pressure changes in a vortex chamber to break material particles along their structural weak points, and thereby create super fine powders. In essence, the mill has been designed to provide efficient, energy-saving fine pulverizing powder using relatively low energy, i.e. the energy invested to pulverize one Kg of powder is much lower than the energy used to pulverize the same amount of powder by conventional jet mills or mechanical (blades or balls) milling while reaching the same particles size (See Table 1).

TABLE 1

Comparison between a jet mill and SFVM (note the difference in energy consumption)

| Mill | Required Air Flow ($m^3$/min) | Pressure Drop (bars) | Feed Rate (Kg/hour) | Kwt × hour/ kg. | Kcal/kg |
|---|---|---|---|---|---|
| Jet Mill | 2.84 | 7 | 20 | 2.360 | 2029 |
| Super Fine Vortex Mill | 1.3 | 4 | 25.6 | 0.483 | 415 |

The design of the SFVM allows for a flexible tuning of the particles size and the size distribution by varying the following parameters:

The input pressure, increasing pressure applied to the inlet of the main mill chamber, would increase the energy inflicted per unit of powder, thus increasing the disintegration of the particles which would lead to decreasing the particles size and narrowing the distribution. However, high energy may lead to a reduction in the biological activity of the final pulverized product.

There are two additional parameters that control the loading rate of the product onto the mill:

(1) The rate by which the product is poured into the mill receiving-funnel (2) The injector pressure.

A high loading rate would decrease the energy per Kg of product, thus the energy absorbed by the particles would be lower, resulting in a smaller number of particle disintegrations that would lead to larger particles. In the majority of the following experiments, the injector pressure was constantly set to 2 bars, which was enough to propel the product into the vortex chamber at any investigated feeding rate. However, there was one exception to the above rule, when the main input pressure was high, >3 bars, the gas injected into the main SFVM produced a vacuum that sucked the large lyophilized powder particles into the mill. The ancillary injection inlet is therefore needed when working at pressures below 3 bars.

Effect of the Milling Parameters

These experiments were carried out, using compressed air at a Dew point of 40° C. under non-controlled temperature or humidity.

Human fibrinogen2 and thrombin powders were shipped to the testing site in the aluminum foil wrapped LyoGuards. The lyophilized cakes were crushed to small particles that passed through a 2 mm SS sieve, using a large spatula. 50 gr of each was loaded onto the SFVM funnel. At low air pressure, an auxiliary pressure gauge was added to the funnel port since the suction at the funnel port was too low to sustain a constant load.

1. Effect of the Milling Parameters on Human Fibrinogen2

Table 2 presents the results obtained when lyophilized human fibrinogen2 was milled at various air pressures and different loading rates.

TABLE 2

Milling lyophilized human fibrinogen2 at various air pressures.

| Run No. | Pressure on the mill (Bars) | Pressure on Injector (Bars) | Loading rate (kg/hour) | D(50), (μm) | D(90), (μm) | Air flow**, (m³/hour) |
|---|---|---|---|---|---|---|
| Experiment No. 1 | | | | | | |
| 1 | 6 | 0 | 0.6 | 4.6 | 8.8 | 90 |
| 2 | 3 | 0 | 0.2 | 4.7 | 8.7 | 58 |
| 3 | 3 | 2 | 2.8 | 10.7 | 30.8 | 69 |
| 4 | 1 | 2 | 3.7 | 43.8 | 87.2 | 35 |
| 5 | 2 | 2 | 2.4 | ND* | ND | 50 |
| Experiment No. 2 | | | | | | |
| 1 | 2 | 2 | 4.2 | 23.1 | 50.7 | 50 |
| 2 | 2 | 2 | 3.0 | 17.5 | 42 | 50 |
| 3 | 6.3 | 0 | 0.4 | 4.3 | 8 | 90 |

*ND = Not Done
**Air flow using air dried to Dew point of 40° C.

All particle size distribution curves (see FIG. 1) exhibit a biphasic peak curve with a small peak at 0.5 to 1 μm and a main peak at around 10-30 μm. It can be noted from Table 2 that only run Nos. 1 and 2 conducted in Experiment 2 have similar size distributions to those of the hand-milled human fibrinogen2 (see Table 2 and FIG. 1). Furthermore, as depicted in Table 3 (Experiment No. 2, runs 1 and 2), the highest fibrinogen recoveries measured either by Clauss or by clottable fibrinogen ($A_{280}$), were achieved when the main parameters were set to a pressure of 2 bars and loading rates of 3 to 4.2 Kg/hour.

TABLE 3

Effect of various milling conditions on the water content and fibrinogen activity of human fibrinogen.

| Run No. | Pressure on the mill (Bars) | Pressure on Injector (Bars) | Loading rate (kg/hour) | Water Content (%) | Fibrinogen (Clauss) (mg/mg solids) | Total protein (mg/mg solid) | Clot. Fibr.* (mg/mg solid) |
|---|---|---|---|---|---|---|---|
| Experiment No. 1 | | | | | | | |
| 1 | 6 | 0 | 0.6 | 5.34 | 0.24 | 0.57 | 0.35 |
| 2 | 3 | 0 | 0.2 | ND | ND | ND | ND |
| 3 | 3 | 2 | 2.8 | ND | ND | ND | ND |
| 4 | 1 | 2 | 3.7 | ND | ND | ND | ND |
| 5 | 2 | 2 | 2.4 | 4.96 | 0.35 | 0.68 | 0.36 |
| Experiment No. 2 | | | | | | | |
| 1 | 2 | 2 | 4.2 | 5.76 | 0.35 | 0.67 | 0.44 |
| 2 | 2 | 2 | 3.0 | 6.13 | 0.33 | 0.64 | 0.44 |
| 3 | 6.3 | 0 | 0.4 | 5.28 | 0.22 | 0.58 | 0.32 |

*Clottable fibrinogen done by the $A_{280}$ nm method.

2. Effect of the Milling Parameters on Thrombin Powder

As found in early experiments when using a conventional jet mill, thrombin activity was relatively insensitive to mechanical sheering and consequently, thrombin was found insensitive to milling parameters when using the SFVM. Therefore the main objective was finding the conditions at which the thrombin particle size distribution would result in a distribution similar to that of human fibrinogen2. Also under consideration was the desire to obtain a particle size distribution that would resemble the hand-milled thrombin. It became apparent in the course of the earlier experiments that thrombin powder is very hygroscopic. Thrombin fine milled powder has a very high tendency to contract moisture. Thus, the smaller the particle's size, the faster the increase in water content of thrombin powder. All the above supports designing a process that will achieve a large particle size of thrombin. However, this size should not exceed the size of human fibrinogen2 so that both products will have the same suspension characteristics in HFE-7000.

TABLE 4

Effect of milling parameters on thrombin particle size distribution

| Run No. | Pressure on the mill (bars) | Pressure on Injector* (bars) | Loading rate (kg/hour) | D(50), μm | D(90), μm | Air flow, m3/hour |
|---|---|---|---|---|---|---|
| 4 | 6 | N.A. | 2.7 | 6.1 | 12.8 | 90 |
| 5 | 2 | N.A. | 1.6 | 10.7 | 29.7 | 40 |

*No injector was used.

It can be noted from Table 4 that the size distribution obtained for Thrombin when low pressure was used resulted in large particle size and in a size distribution which is quite similar to that of human fibrinogen2 (see FIG. 1).

From this stage on, all the routine large scale milling for both human fibrinogen2 and thrombin using the SFVM prototype 1 were targeted to the same parameters: 2 bars in the main mill inlet, 2 bars in the injector and a loading rate of 2 kg/hour.

The prototype was retested again in the actual manufacturing facility using nitrogen and operated under the laminar flow hood.

3. Testing the Milling of Human Fibrinogen2

During human fibrinogen2 milling, the humidity under the laminar flow hood was 22% and the temperature, 22° C. All the manufacturing processes were done aseptically, where the loading rate was targeted towards 2 kg/hour and the injector rate was set to 2 bars. The milled human fibrinogen2 was stored in glass containers at 2-8° C. until testing.

Two batches were subjected to milling: batch #1 was used for milling at 2 bars with an initial activity before milling of 0.30-0.31 mg fibrinogen per mg of solids (fibrinogen has been measured by the method of Clauss) and batch #2, with an estimated initial activity of 0.35 mg/mg (fibrinogen/solids), was used for milling experiments at pressures of 1 and 3 bars.

The average water content was 9.31±0.59% (measured in batch #1) once the powder was crushed into 2 mm particles. The results are summarized in Table 5.

TABLE 5

Effect of nitrogen milling pressure on clottable fibrinogen (by Clauss) and particle size distribution of human fibrinogen2 milled at the manufacturing site.

| Milling pressure (bars) | Clauss (mg/mg solids) | Particle Size (D50) (μm) | Particle Size (D90) (μm) |
|---|---|---|---|
| 1 | 0.36 | 20.4 | 39.1 |
| 2 (average of n = 5) | 0.30 ± 0.01 | 16.6 ± 1.0 | 38.4 ± 1.7 |
| 3 | 0.32 | 10.4 | 28.1 |

Figure 2:
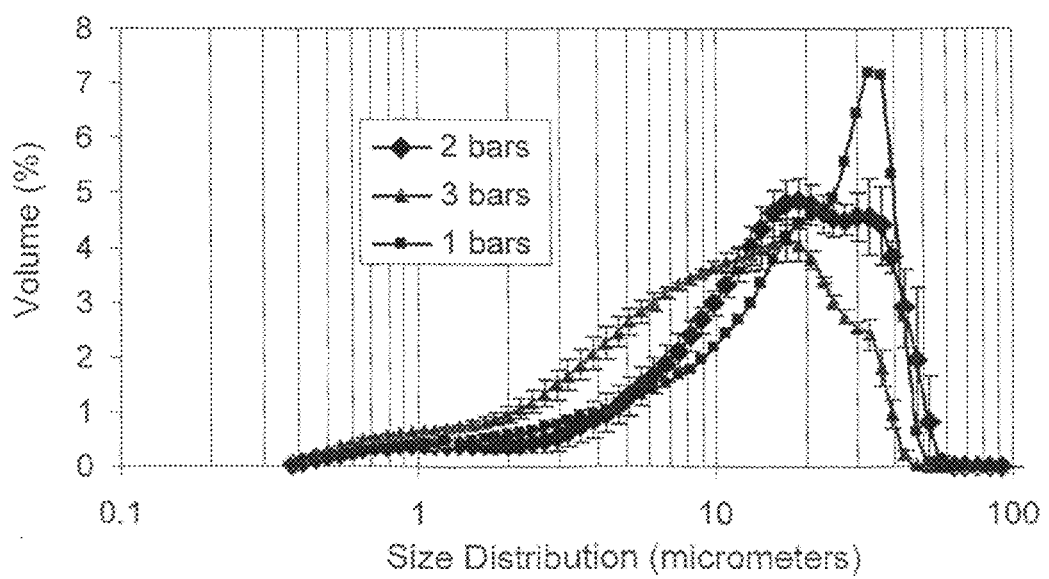
FIG. 2 shows the size distribution profile of human fibrinogen2 milled at various milling pressures.

After milling, the water content was significantly lower (6.66±0.57%), indicating that the milling process also dries the powder. The particle distribution profile changed significantly with pressure (see Table 5—Particle Size D50, and FIG. 2), however, milling at 1 bar still produced a narrow distribution curve similar to the hand mill (compare FIGS. 1 and 2). Furthermore, as can be noted in Table 5, pressures between 1 and 3 did not significantly change the clottable fibrinogen as measured by Clauss.

4. Testing the Milling of Thrombin

During the milling of thrombin, the humidity and the temperature under laminar flow was 26% and 21° C., respectively. All of the manufacturing process was done aseptically. The feeding rate of the 2 mm particles was targeted to 2 kg/hour and the injector rate was set to 2 bars. The milled thrombin was stored in glass containers at 2-8° C. until testing.

Two batches were subjected to milling: Batch #3 was used for milling at 2 bars. Its initial thrombin activity before milling was 25.85±0.21 IU/mg of solids. The average water content was 6.08±0.42% as measured in the 2 mm crushed particles. Batch #2 was used for the milling experiments at pressures of 1 and 4 bars. The water content decreased irrespectively of the pressure once the powder was milled with dry nitrogen. The results show that pressures up to 4 bars did not change the thrombin activity.

TABLE 6

Effect of nitrogen milling pressure on the thrombin activity and particle size distribution of thrombin milled at the manufacturing site.

| Milling pressure (bars) | Water Content (%) | Particle Size (D50) (μm) | Particle Size (D90) (μm) | Thrombin Activity (IU/mg) |
|---|---|---|---|---|
| 1 | 4.35 | 13.0 | 33.6 | 19.7 |
| 2 mean (n = 6) | 4.19 + 0.62 | 10.4 ± 1.4 | 17.5 ± 3.0 | 24.6 + 1.9 |
| 4 | 4.07 | 9.2 | 15.6 | 20.3 |

Figure 3:
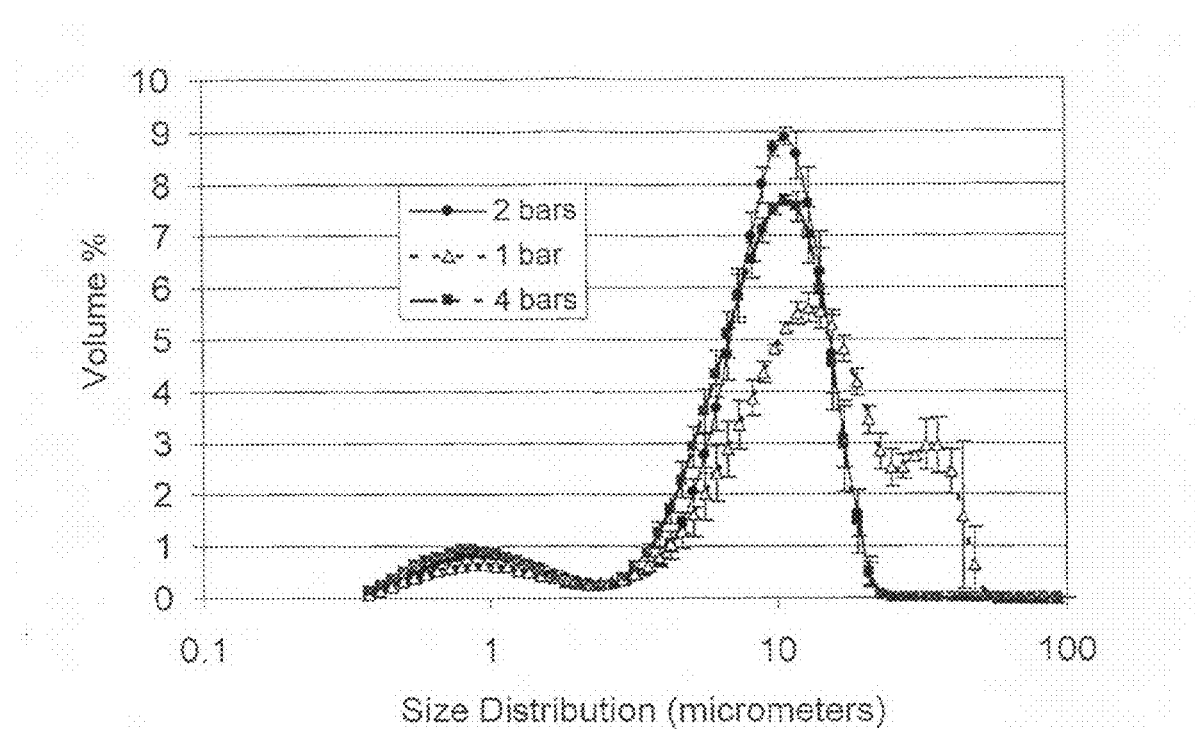
FIG. 3 shows the size distribution profile of thrombin milled at various milling pressures.

It should also be noted that increasing the pressure from 2 to 4 Bars had only a slight effect on the particle size distribution (see Table 6 and FIG. 3).

5. Testing the Repeatability of the Milling Process Using Various Batches of Human Fibrinogen2

Previous experiments involved feeding the SFVM with an uninterrupted succession of LyoGuard® trays while keeping the same main inlet pressure, injection pressure and loading rate. It was conceived that keeping the same milling conditions would result in a comparable product, a powder with the same humidity, size distribution and clotting characteristics. The comparison of two human fibrinogen2 batches each subjected to several milling sessions tested this notion.

Seven LyoGuard® trays, which originated from two human fibrinogen2 batches, were milled separately in the SFVM. Relative humidity in the milling laminar hood was 33% and the room temperature was 22° C.

The water content of the pre-milled lyophilized cakes was similar, 5.48% and 5.45% for batch #4 and #5, respectively. Total protein of the lyophilized cake was almost identical: 0.69 and 0.68 mg proteins per mg lyophilized solids in batch #4 and #5, respectively. Clottable fibrinogen values were also very similar with 0.41 and 0.42 mg/mg solids by the clottable fibrinogen assay ($A_{280}$ nm), in #4 and #5 respectively, and 0.35 and 0.32 mg/mg solids by the Clauss assay. After milling, there was only a small reduction in fibrinogen by an average of 6% (to 0.39 mg/mg solids) as measured by $A_{230}$ nm, or by 20% and 6% (to 0.28 and 0.30 mg/mg solids) as measured by the Clauss method, in #4 and #5, respectively (Table 7 and FIG. 4). No change in the either the humidity or the total protein content was observed in either of the batches (Table 7).

TABLE 7

Reproducibility of two human fibrinogen2 batches (#4 and #5) milled in succession on the same day and under the same milling conditions.

| Batch # | Water Content (%) | Total Protein (mg/mg solids) | Clottable Fib. (mg/mg solids) | Fib. Clauss (mg/mg solids) | Particle Size (D50/D90) (μm) |
|---|---|---|---|---|---|
| 4 | 6.48 | 0.67 | 0.39 | 0.28 | 15.0/35.9 |
| 4 | 4.51 | 0.68 | 0.39 | 0.28 | 17.8/38.6 |
| Average | 5.50 | 0.68 | 0.39 | 0.28 | 16.4*/37.3** |
| SD | 1.39 | 0.01 | 0.00 | 0.00 | 2.0/1.9 |
| 5 | 6.83 | 0.67 | 0.39 | 0.32 | 20.4/41.8 |
| 5 | 4.98 | 0.67 | 0.4 | 0.3 | 19.3/39.5 |
| 5 | 5.25 | 0.67 | 0.38 | 0.29 | 16.8/39.0 |
| 5 | 5.42 | 0.69 | 0.4 | 0.29 | 21.4/44.2 |
| 5 | 6.19 | 0.67 | 0.39 | 0.3 | 17.4/41.3 |
| Average | 5.73 | 0.67 | 0.39 | 0.30 | 19.1*/41.2** |
| SD | 0.68 | 0.01 | 0.01 | 0.01 | 1.9/2.1 |

*Student T-test for D50-p = 0.16
**Student T-test for D90-p = 0.07

Figure 4:
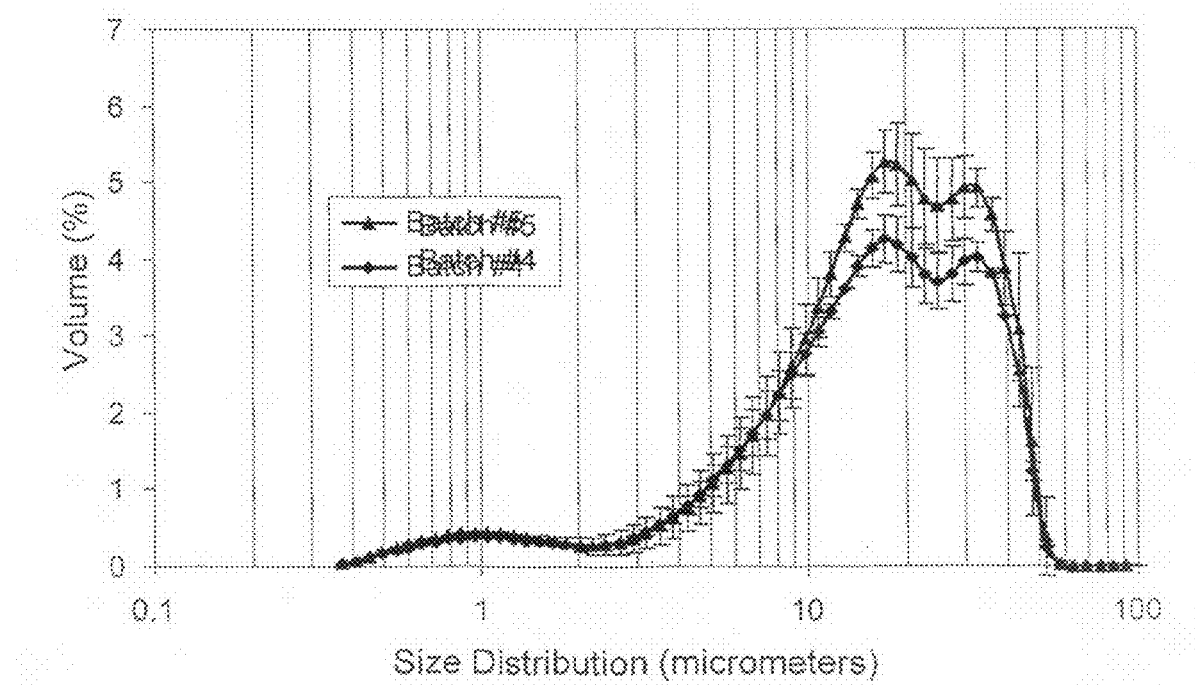
FIG. 4 shows the particle distribution profile of two human fibrinogen2 batches (#4 and #5) milled on the same day using the same standard operation parameters.

Although the mean particle distribution as depicted by the curves D50/D90 was not identical, 16.4 versus 19.1 μm and 37.3 versus 41.2 respectively, these differences were statistically non-significant (see table 7 and FIG. 4).

Figure 5:
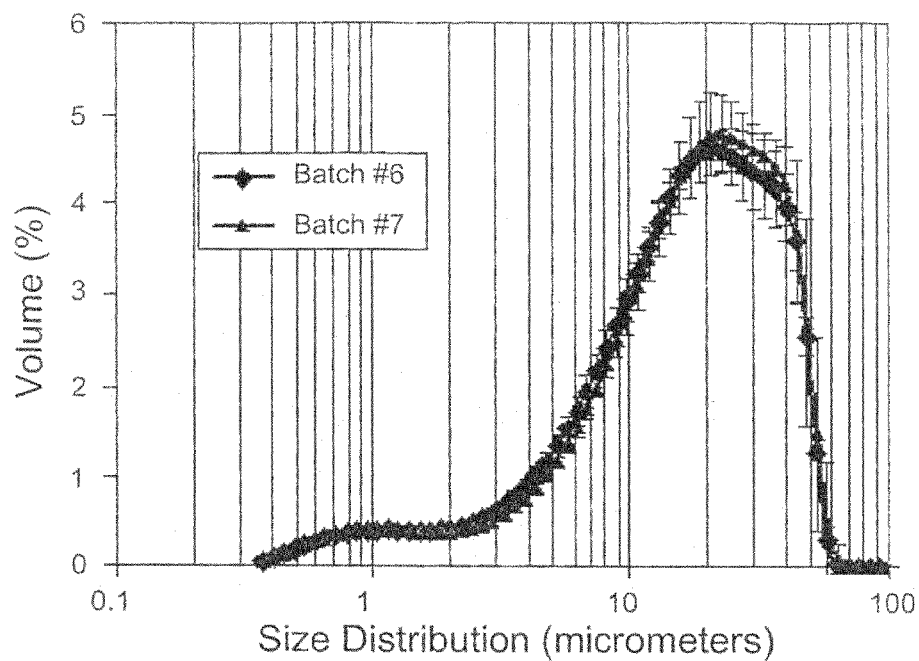
FIG. 5 shows the particle distribution of two human fibrinogen2 batches (#6 and #7) milled in succession on the same day using the same standard operation parameters.
Figure 6:
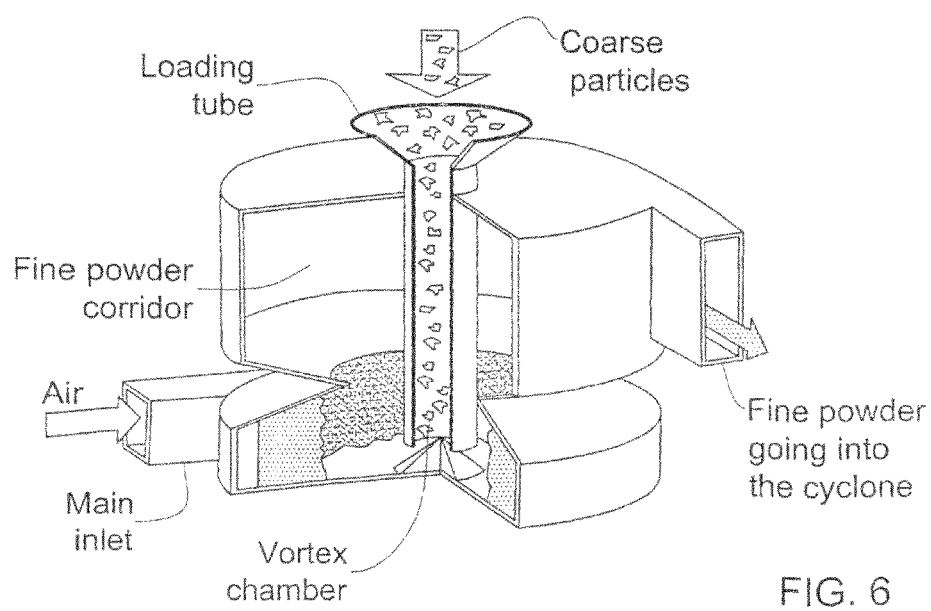
FIG. 6 shows a schematic cut away view of the SFVM.

The repeatability was assessed again, where six LyoGuard® trays originating from two human fibrinogen batches (#6 and #7) were milled in succession (FIG. 5 and Table 8). The relative humidity and the room temperature in the milling laminar hood was 18% and 17° C., respectively.

Total protein of the lyophilized cake was almost identical, 0.65 vs. 0.69 mg proteins per mg lyophilized solids in batch #6 and #7, respectively. Clottable fibrinogen was essentially identical, with 0.39 versus 0.4 mg/mg solids in batch #6 and #7, respectively. A small difference was found between the two batches in the fibrinogen concentration as measured by the Clauss kinetic method, 0.47 versus 0.42 in batch #6 to and #7, respectively. Such variability is very common in measuring fibrinogen by the Clauss assay in highly concentrated fibrinogen solutions. However, only very rarely do fibrinogen readings obtained by the Clauss method exceed the clottable protein ($A_{280}$). After milling, there was no change in clottable fibrinogen (A280 nm), and only small reductions of approximately 11% and 5% were found in fibrinogen measured by the Clauss method, in batches #6 and #7, respectively.

Also, no change in either the water content or in the total protein was observed in any of the batches. Even though the averages of both D50/D90 were not identical in the two batches, 17.9 versus 18.9 μm and 41.5 versus 42.3 μm, in batch #6 and #7, respectively, the size distribution results were statistically identical, P>95% (see Table 8 and FIG. 5).

TABLE 8

Reproducibility of two human fibrinogen2 batches (batch #6 and #7) milled in succession on the same day and by the same milling conditions.

| Batch # | Water Content (%) | Total Protein (mg/mg solids) | Clottable Fib. (mg/mg solids) | Fib. Clauss (mg/mg solids) | Particle Size D50/D90 (μm) |
|---|---|---|---|---|---|
| 6 | 3.80 | 0.65 | 0.39 | 0.44 | 18.7/42.1 |
| 6 | 3.30 | 0.67 | 0.39 | 0.40 | 17.0/40.9 |
| Average | 3.55 | 0.66 | 0.39 | 0.42 | 17.9/41.5 |
| SD | 0.35 | 0.01 | 0.00 | 0.03 | 1.2/0.9 |
| 7 | 3.70 | 0.70 | 0.40 | 0.41 | 18.7/40.5 |
| 7 | 3.80 | 0.69 | 0.39 | 0.41 | 17.6/38.5 |
| 7 | 3.70 | 0.69 | 0.40 | 0.40 | 19.4/46.7 |
| 7 | 3.70 | 0.68 | 0.40 | 0.38 | 19.9/43.4 |
| Average | 3.73 | 0.69 | 0.40 | 0.40 | 18.9/42.3 |
| SD | 0.05 | 0.01 | 0.01 | 0.01 | 1.0/3.6 |

The invention claimed is:

1. A method for micronization of a protein particle dispersion or a dispersion of particles comprising a protein, the protein having a predetermined level of biological activity, the method comprising:

introducing the dispersion into a vortex chamber milling apparatus; and milling the dispersion under milling conditions comprising one or more parameters selected from the group consisting of an input pressure in the range of 1 to 7 Bars, an injector pressure in the range of 0.2 to 5 Bars, a loading rate in the range of 0.1 to 5 kg/hour, and a gas flow in the range of 30 to 100 $m^3$/hour, thereby obtaining a protein powder which retains at least 80% of the predetermined level of biological activity, and has a particle size distribution in the range of 5 to 100 μm or which exhibits a 30 to 400-fold reduction of the original size of the particles in the dispersion.

2. The method according to claim 1, wherein the particles in the dispersion have cracks or cavities.

3. The method according to claim 1, wherein the dispersion is prepared by a freeze-drying process.

4. The method according to claim 1, further comprising mechanically crushing the dispersion before milling.

5. The method according to claim 1, wherein the protein is an enzyme and the biological activity is its enzymatic activity.

6. The method according to claim 1, wherein the protein is a clotting factor.

7. The method according to claim 6, wherein the clotting factor comprises thrombin or fibrinogen.

8. The method according to claim 1, wherein the vortex chamber milling apparatus comprises tangential fluid injection nozzles and performs resonance whirl milling using pressure gradients.

9. The method according to claim 1, wherein the particle size distribution is in the range of 10 to 100 μm or in the range of 10 to 60 μm.

10. The method according to claim 1, wherein at least 90% of the particles following milling are within the particle size distribution.

11. The method of claim 1, wherein the protein powder obtained retains at least 90% of the predetermined level of biological activity.

12. A method for micronization of a protein particle dispersion, the protein having a predetermined level of biological activity, the method comprising:

introducing the dispersion into a vortex chamber milling apparatus; and milling the dispersion under milling conditions comprising an input pressure of 2 Bars; an injector pressure of 2 Bars; a loading rate in the range of 1.6 to 5 kg/hour; and a gas flow rate in the range of 30 to 100 $m^3$/hour, thereby obtaining a protein powder having a particle size distribution of 10 to 60 μm and which retains at least 90% of the predetermined level of biological activity.

13. The method according to claim 12, wherein the vortex chamber milling apparatus comprises tangential fluid injection nozzles which performs resonance whirl milling using pressure gradients.

14. A method for micronization of a protein particle dispersion, the protein having a predetermined level of biological activity, the method comprising:

introducing the dispersion into a vortex chamber milling apparatus; and milling the dispersion under milling conditions comprising an input pressure of 2 Bars; an injector pressure of 2 Bars; a loading rate in the range of 1.6 to 5 kg/hour; and a gas flow rate in the range of 30 to 100 $m^3$/hour, thereby obtaining a protein powder exhibiting a 30 to 400-fold reduction of the original size of the protein particle dispersion and which retains at least 90% of the predetermined level of biological activity.

15. The method according to claim 14, wherein the vortex chamber milling apparatus comprises tangential fluid injection nozzles which performs resonance whirl milling using pressure gradients.

16. A method for micronization of a dispersion of particles comprising fibrinogen and/or thrombin, comprising:

introducing the dispersion into a vortex chamber milling apparatus; and milling the dispersion under milling conditions comprising an input pressure in the range of 1 to 4 Bars, a loading rate in the range of 1 to 5 kg/hour, a gas flow rate in the range of 30 to 100 $m^3$/hour, and optionally an injector pressure of 2 Bars.

17. The method according to claim 16, wherein the milling conditions comprise an injector pressure of 2 Bars.

* * * * *